United States Patent
Romaschin et al.

(10) Patent No.: US 6,203,997 B1
(45) Date of Patent: *Mar. 20, 2001

(54) QUANTITATION OF ANALYTES IN WHOLE BLOOD

(75) Inventors: Alexander D. Romaschin, Etobicoke; Paul M. Walker, Toronto, both of (CA)

(73) Assignee: Sepsis, Inc., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/457,465

(22) Filed: Dec. 8, 1999

Related U.S. Application Data

(63) Continuation of application No. 08/991,230, filed on Dec. 16, 1997, now abandoned, which is a continuation-in-part of application No. 08/552,145, filed on Nov. 2, 1995, now Pat. No. 5,804,370, which is a continuation-in-part of application No. 08/516,204, filed on Aug. 17, 1995, now abandoned, which is a continuation of application No. 08/257,627, filed on Jun. 8, 1994, now abandoned.

(51) Int. Cl.7 .................. G01N 33/53; G01N 33/554; C12Q 1/70; C12Q 1/37
(52) U.S. Cl. .................. 435/7.2; 435/5; 435/7.1; 435/7.24; 435/7.31; 435/7.32; 435/24; 435/34; 435/962; 435/968; 435/975; 436/513; 436/578; 436/536; 436/539
(58) Field of Search .................. 435/5, 7.1, 7.2, 435/7.24, 7.31–7.37, 25, 34, 38, 962, 968, 973, 975; 436/513, 578, 536, 539, 808, 811

(56) References Cited

U.S. PATENT DOCUMENTS

| | | |
|---|---|---|
| 4,647,532 | 3/1987 | Watanabe et al. . |
| 4,737,455 | 4/1988 | De Baetselier . |
| 4,959,302 | 9/1990 | Cornaby et al. . |
| 5,108,899 | 4/1992 | Allen . |
| 5,210,019 | 5/1993 | Margalit . |
| 5,294,541 | 3/1994 | Kaplan et al. . |
| 5,804,370 | 9/1998 | Romaschin et al. . |

FOREIGN PATENT DOCUMENTS

| | | |
|---|---|---|
| 0430440 | 10/1990 | (EP) . |
| 2131948 | 5/1983 | (GB) . |
| WO 90/06514 | 6/1990 | (WO) . |
| WO 92/03734 | 3/1992 | (WO) . |
| WO 92/16553 | 10/1992 | (WO) . |
| WO 94/29728 | 12/1994 | (WO) . |

OTHER PUBLICATIONS

Lilius et al. (1992) J. Biolumines. Chemilumines. 7:117–22.
Michie (1992) Proc. Brussels Symp., pp. 329–38.
Romaschin et al. (1996) Clin. Chem. 42:S130 (No. 146).
Winkelhake et al. (1992) J. Infect. Dis. 165:26–33.
Zeller et al. (1992) J. Leukocyte Biol. 52:449–55.
Ziegler et al. (1991) New England J. Medicine 324(7):429–36.

*Primary Examiner*—Nita Minnifield
*Assistant Examiner*—Padma Baskar
(74) *Attorney, Agent, or Firm*—Klauber & Jackson

(57) ABSTRACT

The invention relates to a method for quantitating the level of a preselected analyte in a sample of blood of a human or animal patient by incubating the test sample with an antibody specific to the analyte to form an immunocomplex, which then interacts with the white blood cell fractions and result in the production of oxidants. Oxidants are detected using chemiluminescent reagents. In addition, the white blood cell oxidant response may be enhanced by the inclusion of certain agents such as opsonized zymosan. As part of the assay, separate blood samples are also maximally stimulated with a maximal stimulatory amount of exogenously-added antigen, and corresponding antibody, to form immunocomplexes, to provide a response factor used in the quantitation of analyte. This quantitative method may be used to determine levels of analytes in a sample of a patient's blood including endotoxin and other analytes related to sepsis, in order to select the proper therapeutic course, or may be used to measure other analytes such as inflammatory mediators, hormones, acute phase proteins, toxins, drugs of abuse, markers of cardiac muscle damage, therapeutic drugs, cytokines, and chemokines.

15 Claims, 2 Drawing Sheets

QUANTITATION OF ANALYTES IN WHOLE BLOOD

CROSS-REFERENCE TO RELATED APPLICATIONS

This application is a continuation of Ser. No. 08/991,230, filed Dec. 16, 1997, now abandoned, which is a continuation-in-part of Ser. No. 08/552,145, filed Nov. 2, 1995, now U.S. Pat. No. 5,804,370, which is a continuation-in-part of Ser. No. 08/516,204, filed Aug. 17, 1995, now abandoned, which is a continuation of Ser. No. 08/257,627, filed Jun. 8, 1994, now abandoned.

FIELD OF THE INVENTION

This invention relates generally to methods to quantitate the level of an analyte in a sample of blood. Analytes may include infectious microorganisms, their toxic products, inflammatory mediators, hormones, acute phase proteins, toxins, drugs of abuse, markers of cardiac muscle damage, therapeutic drugs, cytokines, chemokines, and others.

DEFINITIONS

"Analyte" is defined as the specific substance of interest present in a blood sample and being analyzed by the quantitative assay of the present invention. In the case of analytes related to infection and sepsis, these may include microorganisms and their components, including gram positive cell wall constituents and gram negative endotoxin, lipopolysaccharide, lipoteichoic acid, and the inflammatory mediators that appear in circulation as a result of the presence of these components, including tumor necrosis factor (TNF), interleukin-1 (IL-1) and other interleukins and cytokines. Other analytes may include drugs of abuse, hormones, toxins, therapeutic drugs, markers of cardiac muscle damage, etc.

"Sepsis" is defined as a pathological condition of the body resulting from the presence of infectious microorganisms, which clinically manifests as one or more of the following sequelae: pyrexia, hypotension, hypoxemia, tachycardia, hypothermia, neutrophilia, and neutropenia.

"Antigen" as used in the context of the method of the present invention refers specifically to a material used in combination with an antibody to the antigen to maximally stimulate the production of oxidants by white blood cells. This antigen may or may not be the same as the analyte.

"Immunocomplexes" is a synonym for antibody-antigen complexes.

"Opsonized" refers to a particle to which immunoglobulin and complement factors are bound and which results in a more vigorous recognition of the particle by the immune system. For example, the yeast polysaccharide zymosan, or latex particles, may be opsonized by binding of immunoglobulin and complement factors to their surfaces; opsonized zymosan or latex will stimulate increased oxidant production by white cells after they are activated by exposure to immunocomplexes.

"Response" is a measure of the patient's ability to respond to a maximum stimulatory dose of immunocomplex. It is measured by maximally stimulating the patient's white blood cells with immunocomplexes, versus a control stimulation of antigen only, and expressing the result as the light integral difference between the two tests.

BACKGROUND OF THE INVENTION

Rapid quantitation of specific analytes in an individual's blood is critically important for the diagnosis of disease and its severity, often under emergency conditions, in the monitoring of the progression of pathological conditions and following the recovery process brought about by surgical and drug therapies. It is often important to know not only whether a specific analyte is present, but as well its level, in order to determine the present stage of a particular condition or disease in order to prescribe the most effective remedy at that particular stage. In the treatment of many diseases, a particular therapy may be ineffective or toxic if given at the wrong stage of the condition. For example, the levels of specific markers of cardiac muscle damage and the relationship among them may indicate that a patient has had or may be having a heart attack. The level of a therapeutic drug in the circulation may indicate whether the patient is being dosed optimally, and whether presumptive side effects are indeed due to excess levels of the drug. In infection and sepsis, the circulating levels of infectious microorganism toxins and inflammatory mediators produced by the patient's white blood cells may indicate the severity and level or stage of sepsis and help identify the most efficacious course of therapy. Quantitation of analytes under emergency conditions and using this information to prescribe a particular therapy may mean the difference between saving a patient's life and contributing to the patient's death.

For example, in the case of infection, hospital and particularly intensive care unit patients who have acquired nosocomial infections as a result of peri- or post-operative immunosuppression or secondary to other disease processes, such as pancreatitis, hypotensive or hypovolemic shock, physical trauma, burn injury, or organ transplantation, and develop septic shock syndrome have a mortality which has been quoted to range from 30–70% depending upon other co-incident complications. Despite the development of increasingly potent antimicrobial agents, the incidence of nosocomial infections and, in particular, infections leading to sepsis or septicemia is increasing. The difficulty with many of the promising therapeutic agents is that their window of opportunity and indications for use have not been adequately delineated largely due to a lack of appropriate rapid and quantitative diagnostic procedures and partly due to a lack of complete understanding of the pathogenesis of the sepsis syndrome.

As described in co-pending applications Ser. Nos. 08/552, 145 and 08/516,204, both incorporated herein by reference, the presence of bacteria, viruses or fungi or their cell wall components including gram-positive peptidoglycans, lipoteichoic and teichoic acids, and gram-negative endotoxin (lipopolysaccharide, LPS) in blood is indicative of an infection. In addition, the immune system's reaction to the presence of these foreign antigens by the production of pro-inflammatory cytokine mediators such as interleukin-1 (IL-1), tumor necrosis factor (TNF) and interleukin-6 (IL-6), is also indicative of an infection. The quantity of these analytes in circulation may be used to indicate the severity and level or stage of sepsis. For instance, at an early stage of Gram-negative sepsis, LPS may be present at a concentration as low as 5 pg/ml of whole blood. At the next stage, sepsis has progressed and a mediator of sepsis, TNF, can be detected and measured using antibody against TNF. At stage 3, TNF may be present in smaller amounts since it is transitory and another transitory mediator, IL-1, may appear. As sepsis progresses further, LPS levels may decrease and TNF be absent, but IL-1 may increase and interleukin-6 (IL-6) may appear. Finally, in a more prolonged case of sepsis, LPS may be present and IL-1 may be at low levels but IL-6 may be at very high levels. Thus, diagnosis of sepsis and identifying its stage in the course the disease are critical for the successful treatment of this serious and potentially lethal consequence of infection. Quantitation of the levels of the sepsis-associated analytes provide information necessary to determine the best course of therapy to treat the acute disease.

Until the recent advent of novel therapeutic strategies, sepsis patients have been managed largely by palliative care and administration of antibiotics. The biotechnology industry has facilitated the large scale production of many new targeted biopharmaceuticals which utilize monoclonal antibodies against such initiators of sepsis as gram-negative endotoxin (Centocor's HA-1A(R) or Xoma's Xomen-E5 (R)), tumor necrosis factor (various producers including Hoffman La Roche and Centocor with patents WO 90/06514 and WO 92/16553), interleukins, as well as various soluble receptor antagonists such as IL-1 RA (Synergen) and $sCR_1$ (soluble complement receptor 1)- a truncated recombinant complement regulatory molecule. The cost of these therapeutic agents is significant, being priced at $3,000.00 to $4,000.00 per dose. Thus providing this therapy indiscriminately to patients would add a considerable burden to the health care system without providing a corresponding benefit to patients. In addition, there is need for means to monitor the efficacy of such novel therapies.

Currently, one of the major problems with many of the therapeutic protocols being tested by the pharmaceutical companies conducting clinical trials in sepsis intervention is their inability to rapidly detect early and evolving sepsis. The results of blood cultures may arrive too late. Other septicaemia tests are also time consuming and may not be sensitive enough for early detection. Centocor Inc.'s immunometric assay for tumor necrosis factor-alpha (TNF-α), as described in WO 90/06314, uses two antibodies, one of which is labeled. The National Aeronautics and Space Administration detects Pseudomonas bacteria by extraction of Azurin and detection using Azurin-specific antibody (U.S. Pat. No. 7,501,908). The endotoxin assay kit from Bio Whittaker (Walkerville. Md., U.S.A.) or Seikagaku Kogyo Ltd. (Tokyo, Japan) is a Limulus Amebocyte Lysate (LAL) Assay technique which may be used as a comparison for the present invention.

Many investigators versed in the complexities of the septic response believe that treatment is ineffectual for patients who already manifest the classical clinical symptoms of sepsis (i.e., hyperdynamic circulation, hypotension, decreased systemic vascular resistance, pyrexia and increased oxygen dependency). The course of the inflammatory process has progressed too far for many of the interventions to benefit the patient since the multiple interacting inflammatory cascades with which the body attempts to eliminate the infectious challenge are in many instances at their nadir and difficult to control pharmacologically. Thus, a major clinical and diagnostic challenge is to identify and stage patients, ideally early in the progression of the septic response, or to identity those patients at high risk of developing fulminant sepsis syndrome. The same therapeutic agents given at the one stage in the septic process may have more significant beneficial effects than when given at another, since it is clear that an optimal window period may exist for the efficacy of any particular therapeutic agent. For example, giving a patient antibodies or receptors directed against gram-negative endotoxins when the patient has no detectable levels of these agents present in the circulation and already has a maximally activated cytokine cascade is a waste of resources and of no benefit to the therapy of the patient. The potential market for these anti-sepsis strategies remains large (about 250,000 cases per year in the USA) and has been limited by the inability to identify and stage patients who could benefit from the appropriate pharmacologic interventions.

In addition to infection and sepsis, the diagnosis of many other diseases and conditions are contemplated in the present invention, as their respective diagnostically-useful analytes in circulation can be quantitated by the method of the present invention. Circulating levels of analytes such as hormones, acute phase proteins, toxins, drugs of abuse, markers of cardiac muscle damage, therapeutic drug levels, cytokines and chemokines are among the many clinically useful markers of interest to physicians and other health care professionals, even in an in-home setting, for the diagnosis of and monitoring the treatment of health and disease.

Copending applications Ser. Nos. 08/552,145 and 08/516, 204 describe methods to indicate the presence of a preselected analyte in a blood sample by first forming an immunocomplex between the preselected analyte and an antibody to the preselected analyte which is added to the sample. Sepsis-associated analytes such as endotoxin are used as examples. Any immunocomplex formed as a result then activates complement present in the blood sample which in turn causes neutrophils and other white blood cells present in the blood sample to produce oxidants (see FIG. 1). The oxidants then cause an added chemiluminogenic compound, such as luminol, to release light energy. The white blood cells can be optionally additionally stimulated with the addition of opsonized zymosan or other agents resulting in increased production of oxidants. The amount of light emitted over time can be measured by a luminometer device to indicate the presence of analyte in the sample. A control sample without the addition of antibody may be included, to which may also be added any additional stimulatory agents. This method provides a semi-quantitative determination of the level of the pre-selected analyte in the blood sample.

The present invention is an improvement over that described in the co-pending applications which permits the quantitation of the analyte in the blood sample. The present invention takes advantage of the same method as described in the co-pending application, but to achieve a quantitative determination of the analyte, an additional measurement is made of the maximal response of the patient's white blood cells to immunocomplexes, providing a value to which the chemiluminescence produced by immunocomplexes formed from the preselected analyte is compared. This additional measurement provides the necessary information to render the method of the present invention quantitative and permits the staging of sepsis.

BRIEF DESCRIPTION OF THE INVENTION

This invention is a sensitive, specific and rapid general quantitation method for analytes present in blood. The method is based upon the specificity of antigen-antibody interactions and the high sensitivity of chemiluminescent light emission in response to oxidants produced from the interaction of immunocomplexes with white blood cell fractions in the presence of relevant complement proteins. The invention provides early, diagnostic, quantitative information for analytes such as those indicative of the extent of sepsis and the stage of sepsis. Results are obtained in minutes which is a great advantage over the previous time-consuming methods, for example, of blood culturing for determining sepsis.

To practice the method of the present invention, a blood sample from an individual is obtained, and divided into four aliquots. Two of the four aliquots are used to assess the chemiluminescent response of the white blood cells in the sample to immunocomplexes formed from the binding of any preselected analyte present in the sample with an antibody or antibodies to the preselected analyte which are added to the aliquot, the other aliquot used as a control. The second two aliquots are used to assess the overall response of the white blood cells in the sample to maximal stimulation by immunocomplexes, by adding a large amount of an antigen and its corresponding antibody to one of the aliquots, and only the antigen to the other aliquot as the control. An agent to generally enhance the chemiluminescent response may be added to all of the aliquots, as well as a compound capable of producing light in response to the production of oxidants by white blood cells. Light emission from all four reaction aliquots is measured over a period of time. The amount of light produced by each aliquot is used to calculate the quantity of preselected analyte in the blood sample, based on a preestablished correlation between the amount of preselected analyte in the sample and the ratio between the integrated chemiluminescence of the four samples described above.

The preselected analyte may be selected from any of a number of substances, proteins, and other macromolecules present in blood, such as infectious microorganisms, their toxic products, inflammatory mediators, hormones, acute phase proteins, toxins, drugs of abuse, markers of cardiac muscle damage, therapeutic drugs, cytokines, chemokines, etc. For example, the extent of sepsis or stage of infection in a human or animal patient may be determined by quantitating sepsis-associated markers, such as antigens of Gram-negative bacteria, Gram-positive bacteria, viruses, fungi, or inflammatory mediators such as tumor necrosis factor (TNF), interleukin-1. interleukin-6, interleukin-8 (IL-8). interferons and transforming growth factor $\beta$ (TGF-$\beta$). Hormones may include thyroid hormones and human chorionic gonadotropin. Therapeutic drugs may include digoxin and theophylline. Drugs of abuse may include heroin and cocaine. Markers of cardiac damage may include myoglobin, troponin, and myosin light chain.

The sample may be whole blood or plasma containing white blood cell fractions including neutrophils, lymphocytes and/or monocytes. The agent to enhance chemiluminescence may be zymosan or latex beads and particularly opsonized zymosan or opsonized latex beads. The chemiluminescent compound may be, for example, luminol, lucigenin or pholasin.

The antigen and its corresponding antibody selected to maximally stimulate chemiluminescence may be selected from a wide variety of such combinations such that it stimulates a maximal oxidant response by white blood cells; endotoxin and anti-endotoxin antibodies are preferred. The pair of reaction aliquots containing the antigen/antibody immunocomplexes and the antigen alone provides data on the level of overall maximal response of the patient's white blood cells to a maximal level of stimulatory immunocomplexes. Maximal response is the difference in light emission between a maximal stimulatory dose of immunocomplexes over that induced by antigen alone. The inclusion of a maximum stimulatory dose of immunocomplexes is an important feature of the present invention as it provides a maximal level of chemiluminescence to which that resulting from stimulation of white blood cells by immunocomplexes formed from the analyte is compared in order to quantitate the analyte.

As an example of the practice of the present invention, the preselected analyte is gram-negative endotoxin. A monoclonal antibody of the IgM class directed against the lipid A portion of Gram-negative endotoxin is incubated with one aliquot of a patient's blood. A control containing the patient's blood alone is also prepared. A solution of luminol and then opsonized zymosan is added to both and chemiluminescence is measured for at least 10 to 20 minutes. In addition, to a separate sample of the patient's blood is added a large excess of endotoxin plus a corresponding amount of the IgM monoclonal antibody against endotoxin. A corresponding control sample of the patient's blood contains added endotoxin but no antibody. A solution of luminol and then opsonized zymosan is added to each sample and the chemiluminescence measured over time. The chemiluminescence of the reaction aliquot containing anti-endotoxin antibodies, minus its control, is compared to the chemiluminescence of the reaction aliquot containing excess endotoxin and anti-endotoxin antibody, minus its control. These data are converted to a response factor, which is then correlated with the analyte level in the blood sample based on the preestablished relationship between analyte level and response factor.

In accordance with another aspect of the invention, a diagnostic kit is provided for quantitating a preselected analyte in a patient's blood sample. In one embodiment, the kit may be used to determine the extent of infection in a patient by quantitating an analyte indicative of infection or mediators in response to infection, in a patient's blood sample containing white blood cell fractions comprising:

i) a first container of IgM or IgG antibody specific to an analyte or mediators indicative of infection;
   ii) a second container of chemiluminescent compound;
   iii) a third container of antigen; and
   iv) a fourth contained of anti-antigen antibodies.

An agent to enhance the chemiluminescent response, such as zymosan or opsonized zymosan, latex or opsonized latex, may be included in another container in the kit. The chemiluminescent compound may be, for example, luminol, lucigenin and pholasin. By way of example, if the preselected analyte is endotoxin, the anti-analyte antibody may be IgM antibody against gram-negative endotoxin lipid A. If hepatitis A is the preselected analyte, the anti-analyte antibody may be an IgG antibody against hepatitis A. The antigen and corresponding anti-antigen antibody may be endotoxin and anti-endotoxin antibody. The skilled artisan will be aware of several equivalent components for each of these aspects of the present invention.

It will thus be seen that the process of the invention involves the following steps:

i) providing four aliquots of equal volume of a blood sample in which the level of a preselected analyte is to be determined;
   ii) adding to one aliquot an amount of anti-analyte antibody sufficient to form an immunocomplex with said analyte in the sample;
   iii) keeping one aliquot as a control to the aliquot described in step ii);
   iv) adding to a third aliquot a maximum stimulatory amount of antigen together with an amount of antibody sufficient to form a maximal amount of immunocomplexes with said antibody;
   v) reacting a fourth aliquot with an amount of antigen equal to that added to the aliquot described in step iv);
   vi) optionally adding to all four reaction aliquots an agent to enhance oxidant production, such as opsonized zymosan or latex particles;
   vii) incubating the four reaction aliquots for a time sufficient for any immunocomplexes formed in the samples to react with the white blood cells and complement proteins in the plasma to produce oxidants;

viii) contacting a chemiluminescent compound which reacts with the oxidants to generate light with all four reaction aliquots, prior to or after step vi);

ix) measuring light emission from the four reaction aliquots over a predetermined time period; and x) correlating differences in light emission among the four reaction aliquots to determine the quantity of the preselected analyte in the sample.

BRIEF DESCRIPTION OF THE DRAWINGS

Preferred embodiments of the invention are demonstrated with respect to the drawings wherein.

DETAILED DESCRIPTION OF THE INVENTION

Figure 1:
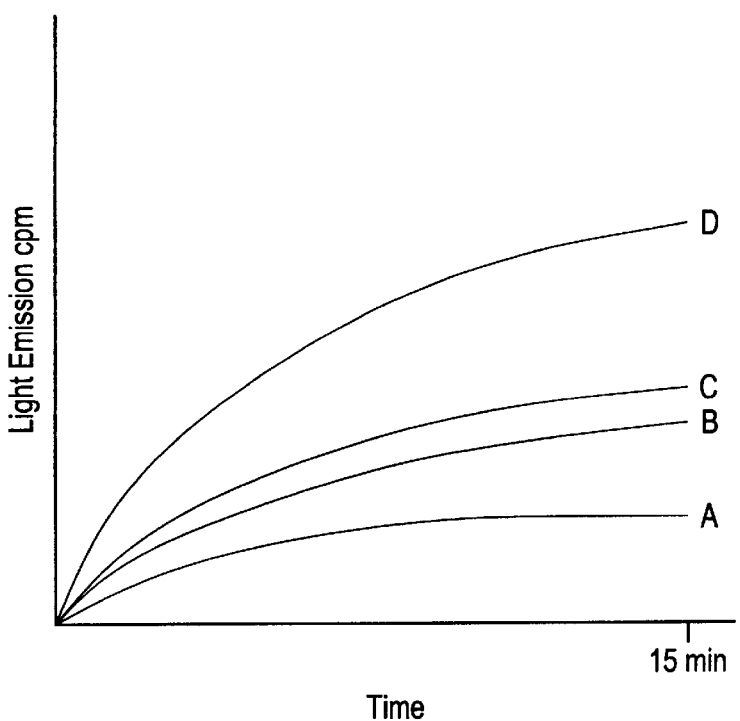
FIG. 1 is a typical whole-blood chemiluminescence profile of a patient with endotoxemia. Curve A represents whole blood plus zymosan; B, whole blood plus zymosan plus anti-endotoxin antibody; C. whole blood plus zymosan plus exogenous endotoxin (800 pg/ml); and D, whole blood plus zymosan plus exogenous endotoxin (800 pg/ml) plus anti-endotoxin antibody.

The invention relates to a method for quantitating the level of a preselected analyte in a sample of blood of a human or animal patient by incubating the test sample with an antibody specific to the analyte to form an immunocomplex, which then interacts with the white blood cell fractions present in the blood sample and result in the production of oxidants. Oxidants are detected using chemiluminescent reagents added to the sample. The white blood cell oxidant response may be optionally enhanced by the inclusion of certain agents such as opsonized zymosan. In order for the assay to be quantitative, separate blood samples are maximally stimulated with an excess or saturating amount of exogenously-added antigen and a corresponding anti-antigen antibody, providing a value of overall maximal response of the patient's white blood cells to immunocomplexes. The ratio between the integrated light output from the sample, minus its control, and the maximally-stimulated sample, minus its control, provides a response factor used in the quantitation of analyte. This quantitative method may be used to determine levels of an analyte in a blood sample, such as endotoxin and other analytes related to sepsis, in order to assess severity and level or stage of sepsis and to direct and monitor the proper therapeutic course. The quantitative assay may also be used to measure the level of other preselected analytes present in a blood sample, such as hormones, acute phase proteins, toxins, drugs of abuse, markers of cardiac muscle damage, therapeutic drugs, cytokines, chemokines. etc. The maximal response calculated from the maximum chemiluminescence of the patient's white cells to a maximal stimulation by immunocomplexes may also be used to indicate the stage of sepsis in conjunction with CLmax, which measures the maximal light emission in the assay sample containing the patient's blood sample without antibody but with opsonized zymosan.

The method described in the present invention improves the utility of the inventions described in the parent applications, Ser. Nos. 08/552,145 and 08/516,204, incorporated herein by reference, in that the method of the co-pending applications is not a quantitative assay. As such, it cannot be used to provide the precise levels of an analyte and therefore has limited diagnostic use where precise analyte levels are necessary, such as in the staging of sepsis or quantitating other analytes. As described above, knowledge of the precise levels of endotoxin and TNF levels in circulation in a sepsis patient can help identify the stage of sepsis and govern the proper course of therapy so as to not exacerbate the patient's condition with an ineffective or inappropriate therapy at a particular stage of the disease. Knowledge of the precise level in circulation of a therapeutic drug with a narrow therapeutic index is important to ensure optimal drug efficacy and avoiding potential side effects.

This disclosure describes an improvement to the prior invention which solves the aforementioned problems. In the parent applications, a blood sample is divided into two aliquots, once receiving antibodies to the analyte, and the other portion serving as a control. To both portions is added a compound which produces light in response to the production of oxidants by white blood cells present in the sample, and to both aliquots is optionally added a white blood cell stimulatory agent such as zymosan or opsonized zymosan. Analyte present in the blood sample forms an immunocomplex with the added anti-analyte antibody, which in turn stimulates the white blood cells in sample to generate oxidants. The oxidants react with the chemiluminescent agent to produce light, which is detected with in a luminometer or similar device. The integrated light output from this sample, less that produced by the control containing all components except the anti-analyte antibody, gives an indication of the presence of the analyte in the blood sample. This resulting light emission profile is shown as curves B and A of FIG. 1. The method of the parent application can be made semi-quantitative by performing several assays using different ratios of blood to anti-analyte antibody, and examining the light production by the samples for the threshold ratio which produces a readout; this is however a tedious method of obtaining more quantitative results. The improved method of the present invention makes possible quantitative determinations which can be performed rapidly and efficiently.

Figure 2:
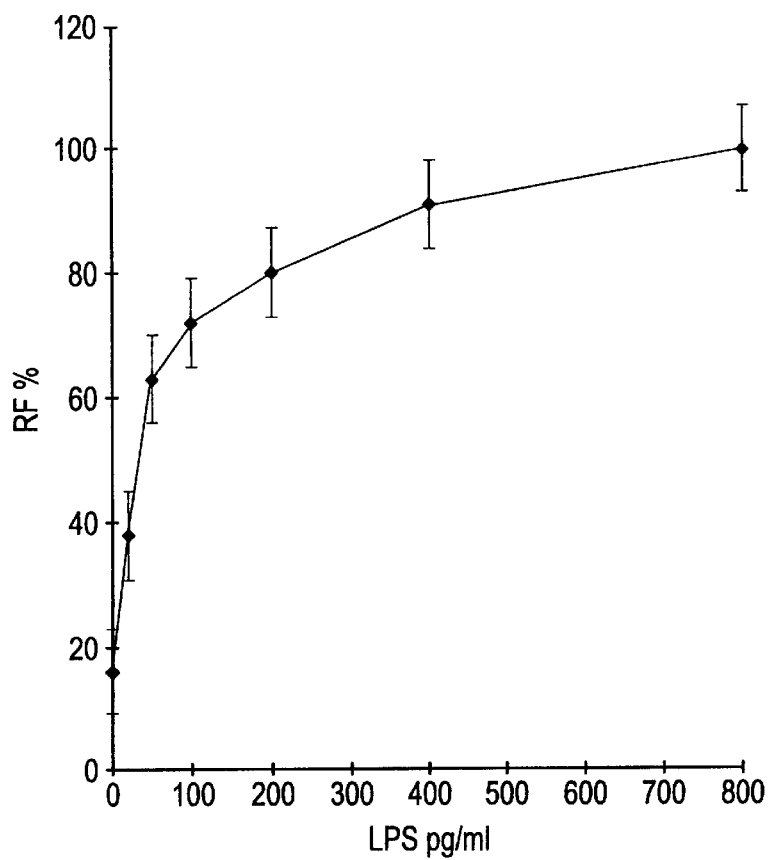
FIG. 2 demonstrates a dose response of endotoxin ("LPS") versus response factor (RF), calculated as $\int(B-A)/\int(D-C)$, where the values A B, C, and D represent 15 minute reaction integrals of the chemiluminescence of the samples depicted in FIG. 1.

The present invention utilizes the same two blood sample aliquots as in the method of the parent application, but includes two additional blood sample portions which are used to measure the maximal response of the patient's white blood cells to immunocomplexes (producing light emission data of curves D and C of FIG. 1). The ratio between the chemiluminescent response of white cells to immunocomplexes formed from the analyte and anti-analyte antibodies and that produced by a maximal amount of immunocomplexes provides a value from which can be calculated the quantity of analyte present in the sample. FIG. 2 shows the dose response to LPS as the analyte, wherein the percent response factor (% RF) is calculated as $100 \times \int(B-A)/\int(D-C)$, where the values A B, C, and D represent 15 minute reaction integrals of the chemiluminescence of the samples depicted in FIG. 1: A represents whole blood plus zymosan; B, whole blood plus zymosan plus anti-endotoxin antibody; C, whole blood plus zymosan plus exogenous endotoxin (800 pg/ml); and D, whole blood plus zymosan plus exogenous endotoxin (800 pg/ml) plus anti-endotoxin antibody. This curve is highly reproducible among blood samples and patients for various test analytes and various test immunocomplexes.

The individual components of the assay are as follows:

Anti-analyte antibody. The antibody against the preselected analyte of the present method is preferably of the IgM class. IgM-analyte immunocomplexes trigger a reaction sequence which results in the stimulation of white blood cell oxidant production via complement pathway activation. The antibody against the analyte can also be of the IgG class. IgG binds to the Fc receptors on white blood cells and can cause a reduction in the chemiluminescence signal. Under these circumstances, there is a decrease in the level of white blood cell activation from the normal level since white blood cells are lysed. This then also provides a semi-quantitative measure of the level of antigen present and shows an especially dramatic drop in white blood cell activation with high levels of antigen or mediator.

Optional white cell stimulant. Although stimulants such as zymosan or latex beads are not required additions to the test procedure, the chemiluminescence produced by immunocomplexes in the test sample is enhanced by such inclusion. Zymosan and latex beads enhance the chemiluminescent response by stimulating concerted white cell oxidant production and phagocytosis. This stimulation can be further enhanced if the zymosan or latex beads are opsonized, through the binding of immunoglobulin G and complement factors (iC3b and C3b). The addition of zymosan or latex acts as an amplification process to increase oxidant production and is preferred in the practice of the present invention, but is not obligatory for the recognition of immunocomplexes by white blood cells. There are many kinds of latex beads depending upon the polymer from which they are prepared, such as polystyrene, styrene divinylbenzene, and acrylic acid polymers; polystyrene is preferred.

Chemiluminescent indicator. The phenomenon of chemiluminescence resulting from the production of neutrophil oxidants is described by Allen, R. C. *Methods in Enzymology* 133:449 (1986) using the acyl azide dye luminol as a light emitting agent. This technique permits the sensitive measurement of neutrophil respiratory burst activation using small numbers of polymorphonuclear leukocytes or later, even white cells in whole blood. Other chemiluminescent dyes which produce light as a result of neutrophil oxidant production have also been identified including lucigenin and pholasin; others will be known by the skilled artisan.

Immunocomplexes to maximally stimulate white blood cells. Inclusion of a measure of the maximal response of the white blood cells in the patient sample to a maximal stimulatory level of immunocomplexes enables the present invention to provide quantitative results compared to the method of the co-pending applications. This measure may be achieved with any antigen and corresponding anti-antigen antibody that achieves the desired stimulation, such as endotoxin and anti-endotoxin antibody. Antibodies of the IgM class are preferred. The antigen may be identical to the analyte, for example, endotoxin.

Assay procedure. In a typical example of the practice of this invention, a sample of a suspected sepsis patient's whole blood may be tested for the level of endotoxin. The blood sample is divided into two pairs of identical aliquots. One pair is used to measure the chemiluminescent response to immunocomplexes formed from the pre-selected analyte combining with a specific anti-analyte antibody; the second pair is used to obtain the overall chemiluminescent response to a maximal concentration of immunocomplexes. The first aliquot of whole blood is mixed with an antibody to endotoxin, preferably with a monoclonal antibody such as Xomen-E5, a murine monoclonal IgM pentamer directed against a lipid A component of gram-negative endotoxin, produced by Xoma, Palo Alto, Calif. In parallel, the second aliquot is used as a control. To measure maximal response with the second pair of blood sample aliquots, to one is added an excess of endotoxin and anti-endotoxin antibody. A control for this sample is prepared containing the added antigen but not the antibody. To all four of the thus-prepared aliquots is added luminol solution and, optionally, complement-activated zymosan or complement-opsonized latex beads.

The chemiluminescent response may be measured in all four reaction aliquots for from about 10 minutes to about one hour. The preferred period is 10 to 20 minutes. After this period, the neutrophils appear to be progressively deactivated or spent with the result that the chemiluminescent response is appreciably decreased and is finally exhausted.

In a preferred aspect of this invention, a small volume of undiluted whole blood (10 $\mu$l or 50 $\mu$l), heparinized (<2 U/ml) or EDTA anticoagulated, and kept at room temperature is employed. A blood sample is incubated with anti-analyte antibody at 37° C. for five to ten minutes. A separate but similar control does not contain the specific anti-analyte antibody. To determine the response factor (RF) and to render the assay quantitative, to one sample of blood is added a maximally stimulating level of an antigen such as endotoxin (800 pg/ml) and corresponding anti-antigen (in this instance anti-endotoxin) antibody; to the control, only the antigen (endotoxin) is added. After incubation of all four samples, 300 $\mu$l of 150 $\mu$M luminol solution is added to all four samples followed by 50 $\mu$l of complement-opsonized zymosan, (2.5–3.0×10$^9$ particles ml). All four samples are placed in a thermostatted (37° C.) luminometer and the luminescence integrated over the test period. The resulting response factor, determined as described above, is used to determine the endotoxin level in the sample by interpolation from the predetermined relationship between endotoxin level and response factor, as in FIG. 2.

In another aspect of this invention, whole blood is first combined with luminol solution and then the various antibodies and antigen are added and the four reaction aliquots incubated at 37° C. for five to ten minutes. Zymosan may then be added.

The examples below describe several methods of practicing the invention, such as varying the order in which to add the reagents, varying blood dilutions, and omitting zymosan. Modifications of these protocols while within the scope of the invention, may be conceived by the skilled artisan. In place of a whole blood sample, a sub-fraction of white blood cells, such as neutrophils or lymphocytes or monocytes, may be used as a substrate. A chemiluminescent compound other than luminol may be used. such as, lucigenin or pholasin.

MATERIALS AND METHODS

Reagents and bacterial products. Luminol (5-amino-2,3-dihydro-1,4-phthalazinedione, free acid), zymosan A (*Saccharomyces cerevisiae*), lipopolysaccharides from *Escherichia coli* (*E. coli*) serotypes (026:B6, 055:B5, 0111:B4) (gram-negative endotoxin), and lipoteichoic acids from *Streptococcus spp.* (Gram-positive cell wall constituent) were purchased from Sigma (Sigma Chemical Co., St. Louis, Mo.).

Chemiluminescence Reagents. Buffer for measurement of whole blood or white cell chemiluminescence studies was HBSS (pyrogen free, endotoxin less than 0.005 EU/ml) containing 1.5 mM calcium salt and 0.9 mM magnesium salt (Gibco BRL. Grand Island, N.Y.). This buffer (500 ml) was vigorously mixed overnight at 25° C. with luminol to yield a saturated solution (150 μM, HBSS-luminol) and then supplemented with 4 U/ml of lithium heparin.

Opsonized Zymosan. To prepare human complement-opsonized zymosan., pooled fresh frozen citrate anti-coagulated human plasma was dialyzed against 4 volumes of 28.5% saturated ammonium sulfate solution for 2 hours at room temperature and then against fresh 28.5% saturated ammonium sulfate overnight at 4° C. The precipitate was removed by centrifugation and the supernatant dialyzed against 2 changes of 10 volumes of HBSS without calcium and magnesium at 4° C. This immunoglobulin-depleted serum fraction (<10% IgG and IgM based on nephelometric assay) was then mixed with a half volume of heat-activated zymosan A (5 g/litre of normal saline) in the presence of 1.3 mM calcium salt and 0.9 mM magnesium salt for 15 minutes at room temperature to opsonize the zymosan. The opsonized zymosan was subsequently washed three times with 2 volumes of ice-cold sterile normal saline and resuspended in its original volume (approx. $3 \times 10^6$ particles per microliter).

Chemiluminescent Assay for Endotoxin. All glass surfaces used for endotoxin assay or storage of reagents for endotoxin assay including assay tubes were depyrogenated by heating to 300° C. for at least 6 hours. All polystyrene and polyethylene surfaces used for storage of antibodies, HBSS-luminol or blood products were sterile and essentially endotoxin free as determined by chromogenic LAL assay of pyrogen free water left in contact with the surface of interest. All pipette tips used for fluid transfer were sterile and pyrogen free (Diamed, Mississauga, Ontario. Canada). Blood samples used for the assay were drawn by venipuncture or through indwelling arterial lines into sterile 3 ml EDTA anti-coagulated Vacutainer tubes (Becton Dickenson, Franklin Lakes, N.J.) which were pretested for LPS content (less than 0.005 EU/ml).

All chemiluminescence experiments utilizing whole blood or blood cell fractions were assayed in triplicate and the results expressed as the mean luminometer counts per minute ±1 SD. In all assays, HBSS-luminol buffer (300 ul) was pre-mixed with 30 ul of antibody solution and subsequently incubated with 10 ul of whole blood or isolated neutrophils in fresh human plasma. After incubation with blood at 37° C. for 5 minutes in a thermostatted aluminum heating block the assay tubes were transferred to the chemiluminometer (E. G. & G. Berthold Autolumat LB953, Wildbad. Germany) for addition of 20 ul of human complement-opsonized zymosan. All assays were incubated at 37° C. in the chemiluminometer for 20 minutes with continuous measurement of light emission from each tube at least every 60 seconds for a minimum 0.6 second counting window. Chemiluminescence reaction curves and integrals were captured using Axis Cellular Luminescence System Software (version 1.03 from ExOxEmis Inc., San Antonio, Tex.).

Example I: Quantitation of LPS

To permit quantitation of endotoxin in whole blood, the following reaction aliquots were set up:

A=Whole blood+zymosan
B=Whole blood+anti-LPS antibody+zymosan
C=Whole blood+exogenous LPS (800 pg/ml)+zymosan
D=Whole blood+exogenous LPS (800 pg/ml)+zymosan+anti-LPS antibody.

All reaction aliquots contained opsonized zymosan in order to optimize oxidant production of the patient's white blood cells in response to immunocomplexes. In addition to the patient's blood sample and zymosan, tube B contained antibody against the analyte to be measured. in this case endotoxin. Tube A served as a control to tube B. In order to determine the maximal response of the patient's white blood cells to immunocomplexes, tube C contained the maximal stimulatory concentration of LPS from E. coli 055:B5 plus anti-endotoxin antibody (determined to be 800 pg/ml or 0.67 EU/ml at an antibody concentration of 0.8 ug/assay); control tube D contained the same amount of antigen but no antibody. While in this example the antigen used to form immunocomplexes to determine maximal response (endotoxin-anti-endotoxin) was identical to the analyte, this does not need to be the true for all analytes. The response factor, $RF = \int(B-A)/\int(D-C)$, was calculated as the difference between the antibody-dependent (tube B) and non-antibody-dependent (tube A) twenty-minute reaction integrals divided by the difference in antibody-dependent (tube D) and non-antibody-dependent (tube C) twenty-minute reaction integrals of reaction mixtures containing a maximal stimulatory dose of endotoxin. A typical whole blood chemiluminescence profile of a patient with endotoxemia is shown in FIG. 1.

The averaged standard %RF curve established with 40 non-endotoxemic blood samples is displayed in FIG. 2. At the antibody concentration employed in the assays depicted in FIG. 2 (0.8 ug protein), a sharp dose-response curve was achieved between 0 and 80 pg/ml, then a more gradual response was seen over a range of 80 to 400 pg/ml with a plateau being achieved at 800 to 2000 pg/ml.

Example II: Comparison with the Limulus Amebocyte Assay (LAL)

Figure 3A:
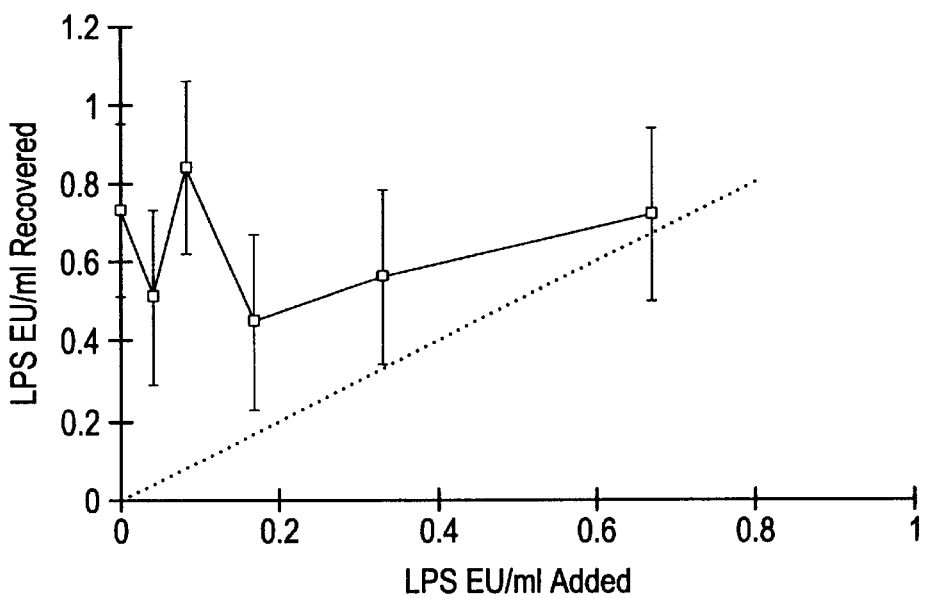
FIG. 3A and FIG. 3B compare (A) the Limulus amoebocyte assay (LAL) endotoxin assay to (B) the method described in the present invention.
Figure 3B:
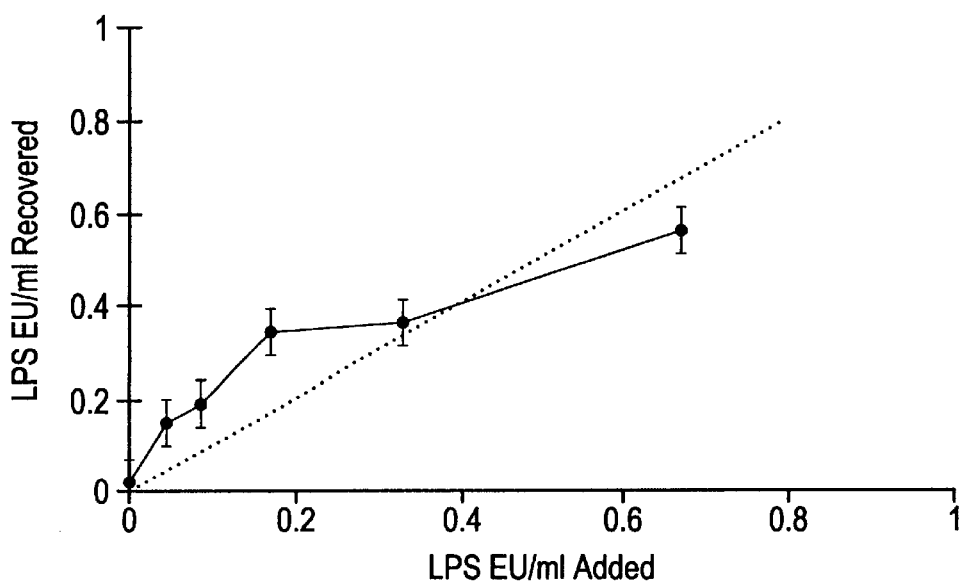

Bland-Altman bias plots were used to compare the chemiluminescent method of the present invention to the LAL method (FIG. 3). Recovery rates from each method were subtracted from true values of added endotoxin. The chemiluminescence assay shows a closer association with the zero bias line than does the LAL assay.

Recovery performance was compared for LPS between the two methods using 50 pg/ml as the cutoff value:

| Parameter | Assay of the present invention | LAL |
|---|---|---|
| sensitivity | 98% | 63% |
| specificity | 100% | 38% |
| positive predictive value | 100% | 75% |
| negative predictive value | 94% | 25% |

The assay of the present invention demonstrated higher sensitivity specificity, and better positive and negative predictive values as compared to the LAL assay.

Example III: Clinical Application of the Assay for Endotoxin Measurement

To validate the utility of whole blood chemiluminescence for quantitating endotoxin levels in patient's blood, evaluating white blood cell immunoresponsiveness, and determining the association between endotoxemia and clinically-important outcomes for critically ill patients, whole blood endotoxin measurements by the method of the present invention were made on 74 consecutive patients upon admission to a medical surgical intensive care unit. A total of 101 patients who met sepsis criteria as defined by ACCP/SCCM consensus were prospectively studied. Daily assays in quadruplicate were obtained.

| Characteristics of Patients by Intensive Care Unit Admission Diagnosis | | | | |
|---|---|---|---|---|
| Diagnosis | Number of patients with diagnosis | Number of patients with Endotoxin >50 pg/ml | Prevalence | Mortality |
| Sepsis patients: | | | | |
| Sepsis | 95 | 64 | 67% | 52% |
| Non-sepsis patients: | | | | |
| Elective Surgery | 21 | 9 | 45% | 0% |
| Single Organ Failure | 14 | 4 | 29% | 29% |
| Post Arrest | 6 | 4 | 67% | 67% |
| Other | 8 | 3 | 33% | 33% |

Control patients (n=30) had no detectable endotoxin. Patents categorized in the non-sepsis group had 226±345 pg/ml endotoxin in the blood. Patents categorized in the sepsis group had 404±354 pg/ml endotoxin (p=0.05 vs. the non-sepsis group).

The following conclusions may be drawn from these data: (1) Endotoxemia is associated with conditions other than sepsis. A significant number of patients not diagnosed with sepsis had levels of endotoxin above 50 pg/ml (for example, 9 of 21 or 45% of patients for elective surgery; 4 of 6 or 67% of post-arrest patients). Patients not diagnosed with sepsis but with endotoxemia exhibited 100% mortality. Therefore, in retrospect, diagnosis of endotoxemia (of >50 pg/ml) with a sensitive quantitative assay would have been critical in identifying patients who would succumb to undiagnosed endotoxemia.

Early, accurate detection of endotoxemia may allow prompt intervention with anti-sepsis, or anti-endotoxin strategies and could result in altering the progression of the inflammatory response through sepsis to organ dysfunction and shock.

Example IV: Measurement of Gram Positive Cell Wall Products

Monoclonal antibodies were raised against a mixture of 6 lipoteichoic acids (LTA) extracted from gram positive bacteria (*Staphylococcus aureus, Bacillus subtilis, Streptococcus faecalis, Streptococcus mutans, Streptococcus pyogenes* and *Streptococcus sanguis*). The IgM antibody-producing clones were propagated in culture and subsequently in murine ascites. Ascitic fluid was collected for evaluation of the ability of antibodies to detect lipoteichoic acids added exogenously to the whole blood of a non-infected normal donor. The following table illustrates a typical dose response curve for the detection of lipoteichoic acids in whole blood. The following reaction conditions were used: Luminol buffer 300 ul, test antibody or control (containing no antibody) 35 ul, patient sample 10 ul, human complement-opsonized zymosan 10 ul. Whole blood was added to either control or antibody containing tubes with luminol buffer followed by incubation at 37 degrees Celsius for 10 min. The assay tubes were then transferred to the luminometer (equilibrated at 37 degrees) and human complement-opsonized zymosan (20 μl) was then added and light emission measured over a period of 20 min. with incubation at 37 degrees. Anti-LTA IgM was prepared by diluting ascites 1:40 with HBSS. Control tubes contained the same dilution of ascites but with irrelevant antibodies.

| Dose of LTA added (pg/ml) | Mean 20 min. Light Integral Difference (antibody tube - control tube) |
|---|---|
| 0 | $1.0 \times 10^5$ |
| 50 | $5.6 \times 10^5$ |
| 200 | $8.6 \times 10^5$ |
| 400 | $10.3 \times 10^5$ |
| 800 | $10.2 \times 10^5$ |

Example V: Detection of Gram Positive Endotoxin Added to Blood

To further evaluate the applicability of the chemiluminescence based assay to detect products of gram positive bacteria the blood of a normal donor was exogenously supplemented with heat killed *Staphylococcus aureus* bacteria and subjected to chemiluminescent assay using anti-LTA IgM antibody. Heat-killed bacteria were prepared by boiling a suspension culture of *S. aureus* for 30 min. in distilled water followed by centrifugation to pellet the killed bacterial and then lyophilization to obtain a powder. In this experiment antibody from anti-LTA clones grown in cell culture (DMEM supplemented with 4% FCS) was used at a total IgM concentration of 10 ug/ml (added in a volume of 35 ul). Control tubes contained an equivalent volume of cell culture medium.

| Dose of Heat-killed *Staphylococcus aureus* (pg/ml) | Mean 20 min. Light Integral Difference (antibody tubes - control tubes) |
|---|---|
| 0 | $0.4 \times 10^7$ |
| 50 | $1.1 \times 10^7$ |
| 200 | $1.86 \times 10^7$ |
| 400 | $3 \times 10^7$ |
| 800 | $4.4 \times 10^7$ |
| 2000 | $4.5 \times 10^7$ |

Example VI: Detection of Gram Positive Endotoxin added to Human Blood

To further evaluate the ability of the chemiluminescence assay to detect products of gram positive bacteria a polyclonal antibody preparation was obtained from mice by immunization with a mixture of heat killed gram positive bacteria comprised of the following organisms: *Staphylococcus aureus, Enterococcus faecalis, Streptococcus pyogenes, Listeria monocytogenes, Streptococcus sanguis, Streptococcus pneumoniae, Staphylococcus epidermitis, Bacillus subtilis*. Mice were immunized with 4 injections of 100 ug/injection and sera obtained for testing in the chemiluminescence assay. The same assay conditions were used as in Example IV except that a 1:1000 dilution of mouse serum was used as a source of IgM antibody in a total volume of 35 ul. A blood sample from a normal healthy donor was mixed with increasing concentrations of heat killed bacteria in vitro. The results of the assay are summarized in Table 3.

| Dose of Heat Killed Bacteria (pg/ml) | Mean 20 min. Light Integral Difference (antibody tube - control tube) |
| --- | --- |
| 0 | $0.19 \times 10^7$ |
| 200 | $34.1 \times 10^7$ |
| 400 | $49.6 \times 10^7$ |
| 2000 | $54.8 \times 10^7$ |

Example VII: Detection of Gram-Positive Bacteria in Patients' Blood Samples

The ability to detect products of gram positive bacteria was also evaluated in two patients with documented gram positive infection and no detectable LPS as determined by a chemiluminescent assay of the present invention for LPS as described in Example III. Both patients had *Streptococcus pneumoniae* in their lungs as determined by bronchoalveolar lavage and the results of the chemiluminescent assay for products of gram positive infection utilizing polyclonal murine anti-serum at a 1:1000 dilution are as follows:

| Assay constituents | Mean 20 min. Light Integral Difference (antibody tube - control tube) |
| --- | --- |
| Patient 1 | $8.5 \times 10^7$ |
| Patient 1 plus 2000 pg/ml heat-killed Gram Positive bacteria | $8.6 \times 10^7$ |
| Patient 2 | $9.14 \times 10^7$ |
| Patient 2 plus 2000 pg/ml heat-killed Gram Positive bacteria | $10.8 \times 10^7$ |

Examples IV through VII demonstrate the ability for the method of the present invention to quantitatively detect gram-positive cell wall constituents.

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

What is claimed is:

1. A method for quantitating the level of a preselected analyte present in a sample of blood of a human or animal patient, said sample comprising plasma and white blood cells, said method sequentially comprising:

i) providing four aliquots of equal volume of said sample, indicated as aliquots A, B, C, and D;

ii) providing aliquot B with an amount of anti-analyte antibody sufficient to form an immunocomplex with said analyte in the sample, to provide reaction aliquot B;

iii) providing aliquot A as a control to reaction aliquot B without said anti-analyte antibody, to provide reaction aliquot A;

iv) providing aliquot D with a maximal stimulatory amount of antigen, together with an amount of anti-antigen antibody of the sane class as that of the anti-analyte antibody sufficient to form an immunocomplex with said antibody, to provide reaction aliquot D;

v) providing aliquot C, as a control to reaction aliquot D, with an amount of antigen equal to that provided in reaction aliquot D, but without said anti-antigen antibody, to provide reaction aliquot C;

vi) incubating reaction aliquots A, B, C, and D for a time sufficient for any immunocomplexes formed in the reaction aliquots to react with the white blood cells and complement proteins in the plasma to produce oxidants;

vii) contacting a chemiluminescent compound which reacts with said oxidants to generate light with reaction aliquots A, B, C, and D, prior to or after step vi);

viii) measuring light emission from reaction aliquots A, B, C, and D over a predetermined time period; and ix) determining said level of said preselected analyte by use of a preestablished relationship which correlates response factor to analyte level, said response factor determined from said light emissions from said reaction aliquots A, B, C, D using the formula $\int(B-A)/\int(D-C)$ wherein said values A, B, C and D represent said light emission from said reaction aliquots, respectively.

2. The method of claim 1 wherein said sample is whole blood.

3. The method of claim 1 wherein said white blood cells comprise white blood cell fractions derived from whole blood, said fractions selected from the group consisting of neutrophils, lymphocytes, monocytes, and combinations thereof.

4. The method of claim 1 wherein an agent capable of increasing oxidant production by white blood cells on exposure to immunocomplexes is included in reaction aliquots A, B, C, and D.

5. The method of claim 4 wherein said agent is selected from the group consisting of zymosan, latex particles, opsonized zymosan, opsonized latex particles, and combinations thereof.

6. The method of claim 1 wherein said chemiluminescent compound is selected from the group consisting of luminol, lucigenin and pholasin.

7. The method of claim 1 wherein said anti-antigen antibody and said antigen are anti-lipopolysaccharide antibodies and lipopolysaccharide, respectively.

8. The method of claim 1 wherein said anti-analyte antibody is a monoclonal antibody of class IgM or IgG.

9. The method of claim 1 wherein said analyte is selected from the group consisting of gram-positive bacteria, gram-negative bacteria, fungi, viruses, gram-positive cell wall constituents, lipoteichoic acid, peptidoglycan, teichoic acid, gram-negative endotoxin, lipid A, hepatitis A, inflammatory mediators, drugs of abuse, therapeutic drugs, and cardiac markers.

10. The method of claim 9 wherein said inflammatory mediator is selected from the group consisting of tumor necrosis factor, interleukin-1, interleukin-6, interleukin-8, interferon, and transforming growth factor $\beta$.

11. The method of claim 1 wherein said analyte is indicative of sepsis.

12. A diagnostic kit for quantitating the level of a preselected analyte present within sample of blood of a human or animal patient, said sample comprising plasma and white blood cells, said diagnostic kit comprising:

i) a first container of IgM or IgG antibody specific to the preselected analyte;

ii) a second container of chemiluminescent compound;

iii) a third container of antigen; and iv) a fourth container of anti-antigen antibodies.

13. The diagnostic kit of claim 12 wherein said analyte is selected from the group consisting gram-positive bacteria, gram-negative bacteria, fungi, viruses, gram-positive cell wall constituents such as lipoteichoic acid, peptidoglycan and teichoic acid, gram-negative endotoxin, lipid A, hepatitis A, inflammatory mediators, drugs of abuse, therapeutic drugs, and cardiac markers.

14. The diagnostic kit of claim 13 wherein said inflammatory mediator is selected from the group consisting of tumor necrosis factor, interleukin-1, interleukin-6, interleukin-8, interferon, and transforming growth factor $\beta$.

15. The diagnostic kit of claim 12 further comprising a container which comprises an agent capable of increasing oxidant production by white blood cells on exposure to immunocomplexes.

* * * * *